(12) United States Patent
Peuker et al.

(10) Patent No.: US 7,607,534 B2
(45) Date of Patent: Oct. 27, 2009

(54) DEVICE FOR STORING AND DISPENSING A FLOWABLE SUBSTANCE

(75) Inventors: Marc Peuker, Schondorf (DE); Arno Hohmann, München (DE); Dieter Poschmann, Starnberg (DE); Kerstin R. Janz, Utting (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/576,910

(22) PCT Filed: Oct. 20, 2004

(86) PCT No.: PCT/EP2004/011876

§ 371 (c)(1), (2), (4) Date: Mar. 16, 2007

(87) PCT Pub. No.: WO2005/040008

PCT Pub. Date: May 6, 2005

(65) Prior Publication Data

US 2008/0003049 A1    Jan. 3, 2008

(30) Foreign Application Priority Data

Oct. 24, 2003  (EP) .................................. 03024398

(51) Int. Cl.
*B65D 69/00* (2006.01)
(52) U.S. Cl. ....................... 206/229; 206/438
(58) Field of Classification Search ............. 222/251, 222/320, 416, 464.3, 464.5, 464.1, 81, 82, 222/74, 498, 499; 383/906; 206/229; 203/438, 203/439, 349, 15.2, 15.3
See application file for complete search history.

(56) References Cited

U.S. PATENT DOCUMENTS

| | | | | |
|---|---|---|---|---|
| 1,707,967 | A | * | 4/1929 | Abbott ................ 222/251 |
| 2,294,224 | A | * | 8/1942 | Daly ................... 215/388 |
| 2,583,821 | A | * | 1/1952 | Du Bois ............... 239/327 |
| 2,848,995 | A | * | 8/1958 | Ryan ................... 604/406 |
| 3,023,937 | A | * | 3/1962 | Matter ................. 222/440 |
| 3,122,139 | A | * | 2/1964 | Jones, Jr. ............. 604/326 |
| 3,184,121 | A | * | 5/1965 | Volckening ........... 222/213 |
| 3,308,824 | A | * | 3/1967 | Gandy ................. 604/540 |
| 3,635,376 | A | * | 1/1972 | Hellstrom ............. 222/107 |
| 3,835,834 | A | | 9/1974 | Brown et al. ............. 128/2 |
| 4,138,036 | A | * | 2/1979 | Bond .................. 222/105 |
| 4,534,509 | A | | 8/1985 | Holzner ................ 239/34 |
| 4,606,734 | A | * | 8/1986 | Larkin et al. ............ 604/84 |
| 4,650,452 | A | * | 3/1987 | Jensen ................. 493/206 |
| 4,880,111 | A | | 11/1989 | Bagwell et al. ........ 206/209.1 |

(Continued)

FOREIGN PATENT DOCUMENTS

DE             31 22 237 A1      1/1983

(Continued)

*Primary Examiner*—Jacob K Ackun, Jr.
(74) *Attorney, Agent, or Firm*—Peter L. Olson (57) ABSTRACT

The present invention relates to a device for storing and dispensing a flowable substance. The device comprises a container comprising a base member and a cover member being sealingly connected with each other along the circumference of the container, a compartment for receiving the substance, and an open ended pocket area into which the substance is transferable from the compartment, and a cannula having an internal passageway being in fluid communication with the pocket for dispensing the substance.

32 Claims, 8 Drawing Sheets

U.S. PATENT DOCUMENTS

| | | | |
|---|---|---|---|
| 4,946,040 A * | 8/1990 | Ipenburg | 383/202 |
| 5,226,564 A * | 7/1993 | Steer et al. | 222/107 |
| 5,239,877 A * | 8/1993 | Suddath et al. | 73/864.62 |
| 5,535,885 A | 7/1996 | Daniel et al. | 206/484 |
| 5,616,337 A | 4/1997 | Kasianovitz et al. | 424/414 |
| 5,660,273 A * | 8/1997 | Discko, Jr. | 206/229 |
| 6,000,848 A * | 12/1999 | Massioui | 383/80 |
| 6,102,252 A * | 8/2000 | Overman et al. | 222/105 |
| 6,105,761 A * | 8/2000 | Peuker et al. | 206/229 |
| 6,116,414 A * | 9/2000 | Discko, Jr. | 206/229 |
| 6,149,579 A * | 11/2000 | Lee | 600/35 |
| 6,264,065 B1 | 7/2001 | Jouillat | 222/94 |
| 6,343,929 B1 | 2/2002 | Fischer | 433/81 |
| 6,612,769 B2 * | 9/2003 | Lee et al. | 401/183 |
| 6,964,656 B2 * | 11/2005 | Saint-Ramon et al. | 604/408 |
| 7,040,483 B2 * | 5/2006 | Inuzuka et al. | 206/219 |
| 7,086,528 B2 * | 8/2006 | Raia et al. | 206/229 |
| 7,097,075 B2 * | 8/2006 | Peuker et al. | 222/94 |
| 7,320,398 B2 * | 1/2008 | Bertl et al. | 206/229 |
| 2002/0076671 A1 | 6/2002 | Evers et al. | 433/90 |
| 2002/0122685 A1 | 9/2002 | Lee et al. | 401/118 |
| 2003/0038040 A1 * | 2/2003 | Bertl et al. | 206/63.5 |
| 2003/0146117 A1 * | 8/2003 | Raia et al. | 206/229 |

FOREIGN PATENT DOCUMENTS

| | | |
|---|---|---|
| DE | 37 17 512 A1 | 12/1987 |
| DE | 298 14 215 U1 | 10/1998 |
| DE | 199 62 436 A1 | 7/2001 |
| DE | 100 56 212 A1 | 5/2002 |
| EP | 0 315 693 A1 | 5/1989 |
| EP | 0 895 943 A3 | 2/1999 |
| EP | 0 895 943 B1 | 2/1999 |
| GB | 1 234 573 | 6/1971 |
| WO | WO 96/03326 | 2/1996 |
| WO | WO 98/01360 | 1/1998 |
| WO | WO 98/09605 | 3/1998 |
| WO | WO 02/22466 | 3/2002 |
| WO | WO2005/040008 A1 | 5/2005 |

\* cited by examiner

Dispenser part

DEVICE FOR STORING AND DISPENSING A FLOWABLE SUBSTANCE

CROSS REFERENCE TO RELATED APPLICATIONS

This is a national stage filing under 35 U.S.C. 371 of PCT/EP2004/011876, filed Oct. 20, 2004, which International Application was published by the International Bureau in English on May 6, 2005, which claims priority to EP 03024398.4, filed Oct. 24, 2003.

FIELD OF THE INVENTION

The present invention relates to a device for storing and dispensing a flowable substance. In particular, the present invention relates to a device for storing and dispensing a flowable liquid being a dental substance for tooth treatment.

BACKGROUND OF THE INVENTION

For storing and applying a small quantity of a liquid, a commercially available device includes a container in the form of a so-called "blister package". Two separate recesses are formed in a deep-drawn part of the package which is closed by a removable sheet. Upon removal of the sheet, the two container recesses are exposed so that a brush can be taken out and used to apply the liquid to the treatment site. For example, U.S. Pat. No. 6,105,761 discloses a device for storing and dispensing quantities, particularly small quantities, of one or more flowable substances. The device comprises a pocket which is formed so as to receive an application instrument. The application instrument, which is stored in a pocket of the container or is inserted into the pocket by the user, may be contacted with the flowable substance without opening the container as a whole. It is only necessary to withdraw the application instrument, after it has taken up the substance, from the pocket of the container and move it to the treatment site.

A different example of a conventional single patient dose medicament dispenser with applicator is shown in WO 96/03326.

Such devices are already proven in the market as a cheap and reliable delivery system for storing, mixing, and applying of flowable liquid materials using, for example, such a brush applicator. For indications requiring a higher volume of liquid for the treatment a brush may be, however, disadvantageous because the amount of liquid which can be transferred from the package to the location of treatment is limited to the absorbability of the brush. Furthermore, once a brush is wetted with liquid, the absorbability decreases tremendously, thus becoming nearly useless for transferring further liquid.

SUMMARY OF THE INVENTION

It is an object of the present invention to provide an improved and simplified device for storing and dispensing a desired amount of a flowable substance.

The present invention provides a device for storing and dispensing a flowable substance comprising (i) a container comprising (1) a base member and (2) a cover member being sealingly connected with each other along the circumference of the container, (3) at least one compartment for receiving said substance, and (4) an open ended pocket area into which said substance is transferable from said at least one compartment, and (ii) a cannula having an internal passageway being in a fluid communication with said pocket for dispensing said substance.

According to a first preferred aspect of the present invention, the cannula is a separate component having a first (rear) end and a second (front) end, said first end being associated with said open end of said pocket area. In this preferred embodiment, the cannula is, for example, a moulded part that is incorporated into, i.e., connected to said container.

Preferably, the extension part has a cross-sectional shape comprising sharp edges in the plane between the base member and the cover member, and more preferably comprises a rhombic, triangular or fin-like cross-sectional shape. This cross-sectional shape (in a plane perpendicular to the longitudinal axis of the cannula) of the extension part provides a smooth transition between the extension part and the surrounding base and cover member, and the sharp edges help to avoid hollow spaces between the base member and the cover member, because the sharp edges lie in the plane between the base and the cover member.

Preferably, the extension part has a cross-sectional shape comprising sharp edges in the plane between the base member and the cover member, and more preferably comprises a rhombic, triangular or fin-like cross-sectional shape. This cross-sectional shape (in a plane perpendicular to the longitudinal axis of the cannula) of the extension part provides a smooth transition between the extension part and the surrounding base and cover member, and the sharp edges help to avoid hollow spaces between the base member and the cover member, because the sharp edges lay in the plane between the base and the cover member.

Alternatively, the extension part comprises at least one portion having an increased diameter. Thus, the extension part is a "plug-like" extension part comprising one or more circumferential flanges. Such a structure also avoids hollow spaces between the base member and the cover member since the plug part of the cannula is inserted into said pocket, for example, by press fit, thus stretching the base and cover member around the extension part.

In accordance with a further alternative, the extension part comprises a portion being tapered along the length thereof, with the thickness of the tapered portion decreasing towards said first end. With this arrangement, fluid communication between the pocket and the cannula is provided by attaching the base member and cover member of the container onto the tapered portions or areas, respectively, on the extension part. Preferably, the tapered portion comprises an U-shaped sealing area on each of the opposing surfaces of the tapered portion, wherein the legs of the U-shaped sealing areas extend towards the first end of the cannula, i.e. towards its rear end, and are connected with each other at the edge of the first end. Thus, the two sealing areas are connected with each other and thus extend from one side of the tapered portion to the other side. A passageway is thus formed at one side of the extension part, starting at the edge of the extension part, i.e., between the legs of the "U", and extending towards the bottom of the "U" at that side where the internal passageway of the cannula is accessible.

It is preferred in all alternative embodiments that the first end of the cannula is attached to said open ended pocket by a heat seal, a press fit, and/or an adhesive.

Alternatively, the cannula comprises at its first end an extension part adapted for being attached to the outer surface of the container, and preferably to the cover member. For example, the extension part comprises a disk-like shape. Preferably, the disk-like extensions part is attachable at one surface thereof to the container, and comprises the cannula at the opposite side. Thus, the internal passageway of the cannula also passes through the extension part.

Preferably, the extension part is attached to the container by an adhesive or glue, respectively, which is, for example, is provided in the form of a ring at a certain distance around the passageway opening at the first end. Preferably, the ring of glue is applied on the surface of the (e.g. disk-shaped) extension part. Alternatively, the extension part comprises a recess, preferably ring-shaped, in the surface that is to be attached to the container; the recess receives the adhesive. The latter alternative is advantageous in that it prevents closing of the passageway by the glue. This can be further enhanced in that the part of the extension part surrounding the passageway outlet is somewhat raised relative to the rest of the surface of the extension part, and the recess surrounds the raised part.

The advantage of having a "dispenser part" being formed by the cannula and the extension part that is attachable to the container is that the container, for example a blister package, can be manufactured using existing equipment and existing processes. This provides proven quality of the container. The pre-manufactured container can then be combined with the "dispenser part" in a downstream step of the manufacturing line.

It is preferred that the cannula is inclined with regard to the extension part. That means, for example in case of a disk-shaped extension part, the cannula does not perpendicularly extend from the surface of the extension part but is slightly inclined relative to the plane of the extension part. More preferably, the extension part comprises a bend so that it comprises two portions that are inclined relative to each other. Most preferably, the bend is provided such that the entire assembly of cannula and extension part comprises a zig-zag-configuration. Such a zig-zag-configuration facilitates manufacturing of the dispenser part by injection molding. Furthermore, it allows the entire device to be built as a non-angled device which can be handled by a user like a pen when a liquid is to be dispensed.

In case the extension part is attached to the cover member of the container, fluid communication is established, for example, by puncturing the cover member, for example by a small needle. It is preferred that the size of the hole in the cover member is smaller than the passageway of the cannula because then a controlled dispensing of the substance is achievable. Furthermore, unintended all at once emptying of the container is prevented.

Preferably, the extension part provides a gripping function so that the dispensing device can be gripped by the user at the extension part.

According to a second aspect of the present invention, the cannula is integrally formed with said base member. In other words, the base member and the cannula are provided as a single component of the container, so that the pocket area is a part of the integrally formed cannula.

According to a third aspect of the present invention, the cannula is attached to the cover member, whereby fluid communication is established through the cover member. This aspect is advantageous because the cannula can be attached to the cover member prior to the assembly of the whole device, thus being attached at an early stage of the manufacturing process. According to a first preferred embodiment of the third aspect of the present invention, the cover member is closed to the internal passageway of the cannula in order to properly seal the container. For this reason, a punching member is accommodated in the passageway of the cannula in order to punch the cover member prior to use of the device. Alternatively, a hole or slit is cut into the cover member during the manufacturing process. A slit is preferred since there is no risk that material cut out of the cover member remains in the interior of the container.

As an option for all aspects of the present invention, the cannula comprises a dosing structure, preferably having a variable or flexible volume, like a bellow, to squeeze the substance out of the cannula. The dosing structure is preferably attached to the cover member, and a passageway between the dosing structure and the pocket area is established prior to use, for example, by a punching member. Alternatively, a cartridge with a piston is provided.

According to a preferred embodiment of the present invention, the cannula further comprises an applicator at the second (front) end of the cannula for applying the substance to a target or treatment area. Preferably, the applicator comprises bristles that are (preferably integrally) formed at the second end of the cannula to form a brush for applying dispensed material. In case the bristles are integrally formed with the cannula tip, it is possible to mould the bristles and to stretch the bristles within the injection moulding tool during mould opening. Alternatively, the applicator comprises a foamed material (like a sponge), a non-woven material, or a plurality of fibres (like a felt-tip pen) integrated into the second end of the cannula. The sponge is preferably an open-porous sponge, e.g., made of polyethylene. Such a sponge could easily be sealed within the device. The use of a felt-tip pen-like applicator tip is advantageous due to its stiffness compared to bristles. Moreover, the sealing of the entire device would be facilitated compared to the use of bristles.

In order to avoid foaming or too rapid flow of the liquid through the cannula (for example owing to a sudden activation of the device), the internal passageway of the cannula preferably comprises flow resistors, for example formed by structured surfaces, constricted portions, and/or orifices.

According to a further preferred embodiment, the extension part further comprises stiffening elements, preferably extending away from said extension part. Most preferably, the stiffening elements extend beyond the first end of and away from the cannula, like feelers. Alternatively, or in addition, the base member is strengthened or stiffened by a stiffening structure.

The extension part is preferably formed such that the opening of the internal passageway of the cannula opens at a side surface of the extension part, i.e., offset from the longitudinal axis of the cannula. Such an arrangement of the passageway opening is advantageous for the manufacturing process because it facilitates ejection of the cannula from the mould.

According to a preferred embodiment, grooves are provided in the surface at which the passageway opening is located. The grooves extend from the passageway opening towards the end of the cannula, and provide flow channels between the pocket area and the passageway.

In all aspects of the present invention, it is preferred that the base member is formed as a sheet. Preferably, the base member sheet is a deep-drawn sheet formed of a polypropylene layer, an aluminium layer, and a polyethylene layer. It is also preferred that the cover member is formed as a sheet, and is preferably formed of a polyethylene terephthalate layer, an aluminium layer, and a polyethylene layer. In both sheets, a polyethylene terephthalate layer may be provided between the aluminium layer and polyethylene layers. The sheets used are such that they act as a diffusion barrier with respect to the substance to be received in the compartment. Both of the sheets are preferably flexible, which is useful in that the container, being made of just two flexible sheets, is inexpensive in terms of material and manufacture. Using suitable sheets will safely avoid any diffusion of the compartment content. Thus, the sheet package may be used without any further envelope as a primary package which allows clear marking due to its flat and relatively large-area shape. The separation between the compartment containing the flowable substance and the pocket receiving the cannula is preferably achieved by mutual adherence of the two sheets. The adherence may be created simultaneously with the sealing of the compartment upon filling.

The cover member is alternatively formed as a plastic part, preferably as an injection moulded part that has the same shape like the punching contour of the base member in order to achieve an improved stiffness, and to improve the entire handling of the device. If in this case a two- or multi-component base member is used, the plastic part forming the cover member needs to be foldable between the two compartments, for example by a line of weakness forming a hinge. It is preferred that additional locking structures (for example brackets or clips) are provided that prevent that the folded plastic part is unfolded again after mixing and dispensing of the substance. In order to reduce the tendency to fold back, the used material preferably comprises wax components.

Such locking structures are also preferred for the other embodiments in case materials are used for the base member and cover member having a certain inherent return movement tendency.

The material used for the base and cover sheets as well as for the injection moulded part preferably comprises COC (cyclo olefin copolymer) in order to optimise the barrier properties, i.e. the storage stability. Furthermore, barrier coatings are preferably used, such as metallizing (a coat of vaporized material), or anorganic-organic hybrid polymers.

The sheets or moulded parts are preferably adapted to block light of a particular wavelength range, and are otherwise transparent. For example, materials are used that block light in the range of 300 to 500 nm (blue light).

In a preferred embodiment, the device further comprises a portion separating said compartment from said pocket, said separating portion comprising a passage area adapted to be selectively opened by pressure effective on said passage area for placing said compartment in communication with said pocket. In the device of the present invention, the flowable substance, which may be a liquid or a powder, is made accessible without requiring any tool, by selectively opening the passage area, whereby the substance contained in the compartment is transferred to the pocket for dispensing. The structure of the invention acts as a metering device for dispensing and applying quantities of the substance which are determined by the volume of the compartment.

In a further preferred embodiment of the present invention, the device further comprises two compartments for holding different substances, and a passage area adapted to be selectively opened for placing said compartments in communication with each other. This arrangement is specifically suited for substances to be mixed from components which react with each other. A zone of reduced lateral width may be provided between the compartments to facilitate the compartment which is emptied first to be bent upon the second compartment, thereby preventing the substance from flowing back into the first compartment.

In case two or more compartments are present, the device is activated as follows. First, the passage area between the compartments is opened so that the compartments can communicate with each other. During mixing of the substances contained in the compartments, the separation portion separating the pocket from the compartments is still closed. Only upon proper mixing of the substances, the passage area of separating portion is finally opened so that the resulting substance can be dispensed.

It is to be noted here that typical applications require two- or multi-component devices so that typically devices having two or even more compartments are used. Usually, it is intended to separate the individual substances or components from each other since they may undergo an undesired chemical reaction. The components are brought in contact and mixed with each other only immediately prior to dispensing. However, the present invention is not limited to a two- or multi-component dispensing device.

A plurality of juxtaposed units may be formed in the sheets, each unit including a container and a cannula, the units being inter-connected along tear-off lines. This embodiment results in a further simplification of the storage.

Preferably, the container is pre-filled. Further preferably, the container is part of a set that also comprises a separate applicator like a brush. As a further preferred option, the different juxtaposed units comprise different substances.

In accordance with a further preferred embodiment of the present invention, the cannula comprises a mixer. In a first alternative, the mixer includes mixing elements that provide a static mixer, for example mixing helixes or elements providing flow resistance; these cause a mixing of the substances by swirl or turbulence. The elements providing flow resistance are preferably formed in the form of protrusions or indentations on the inner surface of the cannula (i.e., in the flow channel). These are preferably formed by embossing, coating, cutting or the like. According to a further alternative, the flow passage through the cannula is meandering, i.e., the direction of flow changes along the length of the cannula.

BRIEF DESCRIPTION OF THE DRAWINGS

The present invention is now described with reference to the accompanying drawings, in which.

DETAILED DESCRIPTION OF THE PREFERRED EMBODIMENTS

Figure 1:
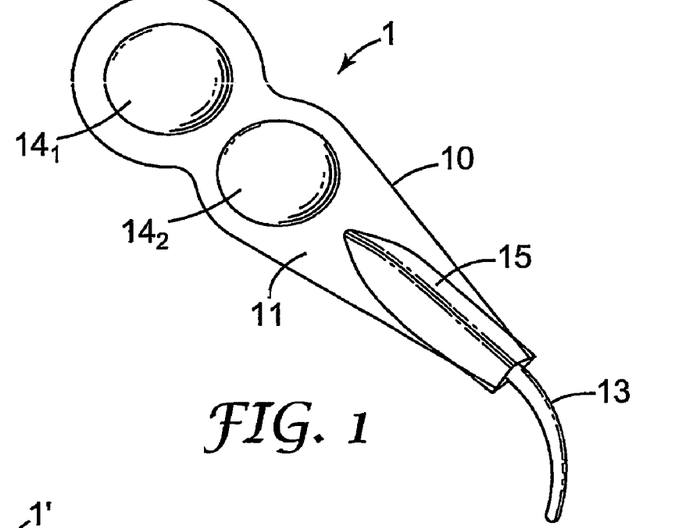
FIG. 1 shows a preferred embodiment of the device according to the present invention comprising two compartments for containing substances, and an incorporated cannula.
Figure 3:
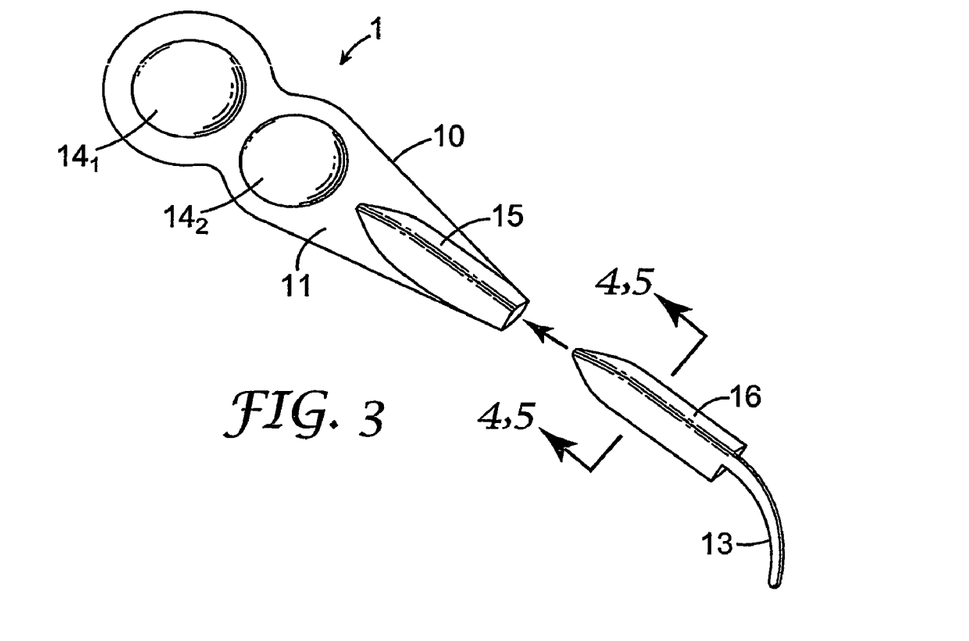
FIG. 3 shows the embodiment of FIG. 1 prior to insertion of the cannula with its extension part into the pocket of the device.

The storage and application device according to a first preferred aspect of the present invention is shown in FIGS. 1 and 3. The device 1 comprises a container 10 that is in this preferred embodiment formed by a deep-drawn sheet 11 and a cover sheet 12 (cover sheet 12 is shown, for example, in FIGS. 4 and 5). Sheet 11 comprises two cushion-shaped compartments $14_1$ and $14_2$ holding a supply of two different flowable substances. Adjacent to the area containing the compartments, a pocket 15 is provided for receiving a cannula 13, in particular an extension part 16 of cannula 13.

FIG. 3 shows cannula 13 with extension part 16 prior to its insertion into pocket 15 of device 1. FIG. 1 shows the assembled storage and application device 1.

The cannula 13 comprises an internal passageway that allows liquid to be dispensed from the compartments $14_1$, $14_2$ through the cannula onto a treatment area. The extension part 16 provided at a first end of cannula 13 provides a tight connection between the cannula and the container 10 of device 1.

Tight mutual connection of the sheets 11 and 12, i.e. the base member and the cover member, is preferably achieved by heat sealing or gluing.

Figure 2A:
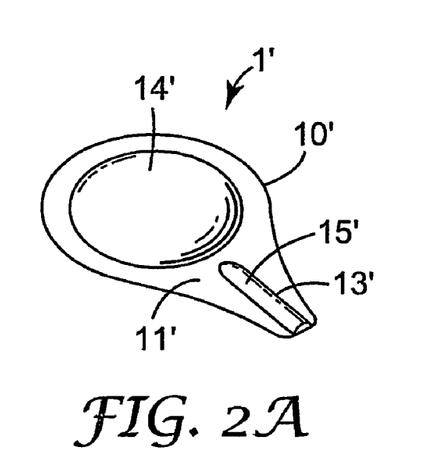
FIG. 2A shows an alternative embodiment of the device according to the present invention comprising a single compartment and an integrally formed cannula.
Figure 2B:
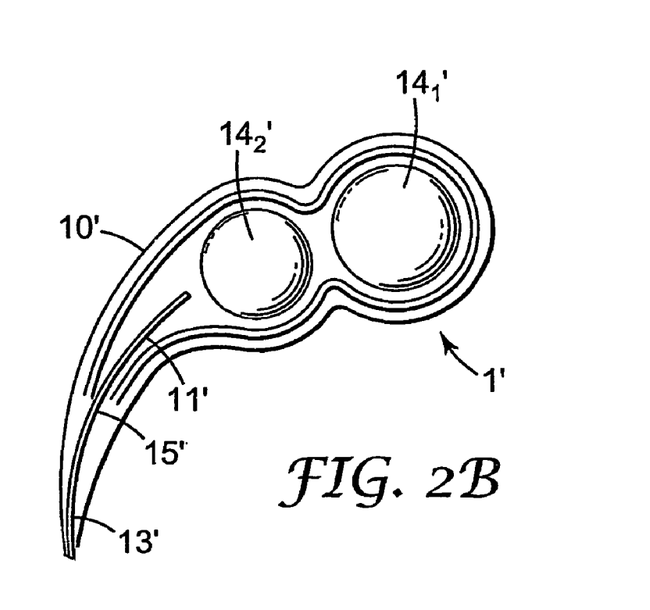
FIG. 2B shows a further alternative embodiment of the device according to the present invention comprising two compartments and an integrally formed cannula.

According to an alternative aspect of the present invention, device 1' comprises a container 10' that is formed by base member 11' and a cover member, as shown in FIGS. 2A and 2B. According to this aspect of the present invention, the cannula 13' is integrally formed with the base member 11', i.e. the cannula 13' is not a separate component that is added to the container 10' at some point of assembly, but forms an elongate extension of the channel-like pocket area 15'.

According to FIG. 2A, the container 10' comprises a single compartment 14' only. Alternatively, as shown in FIG. 2B, two compartments $14_1'$ and $14_2'$ can be provided for containing different substances.

In order to achieve a tight seal not only between the base member and the cover member, i.e. the two sheets, but also in the pocket area where cannula 13 is incorporated into device 1, the extension member 16 comprises an increased cross-section, as shown in FIGS. 4 through 8.

Figure 4:
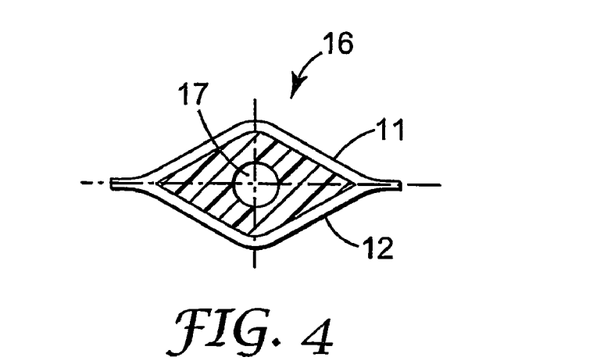
FIG. 4 shows a preferred cross-sectional structure of the extension part of the cannula.

According to a first alternative design, the extension part 16 comprises a rhombic cross-section (see FIG. 4). This increased cross-sectional portion of cannula 13 (with internal passageway 17) is finally accommodated between base member 11 and cover member 12.

Figure 5:
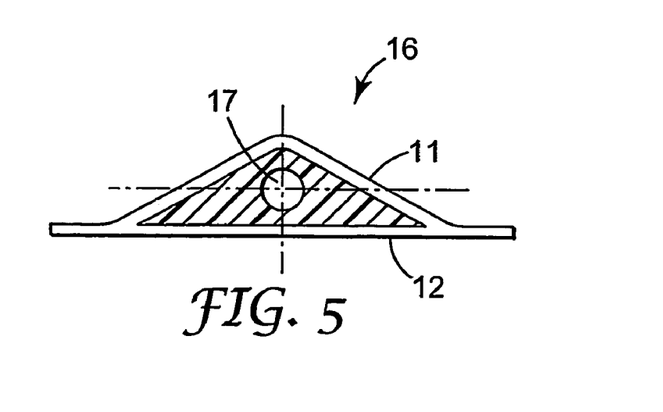
FIG. 5 shows a further preferred cross-sectional structure of the extension part of the cannula.

FIG. 5 shows a different embodiment of extension part 16. According to FIG. 5, extension part 16 has an increased cross-sectional area in the form of a semi-rhombus (compared to FIG. 4), or triangle, respectively. Extension part 16 is tightly accommodated between base member 11 and cover member 12.

Figure 6A:
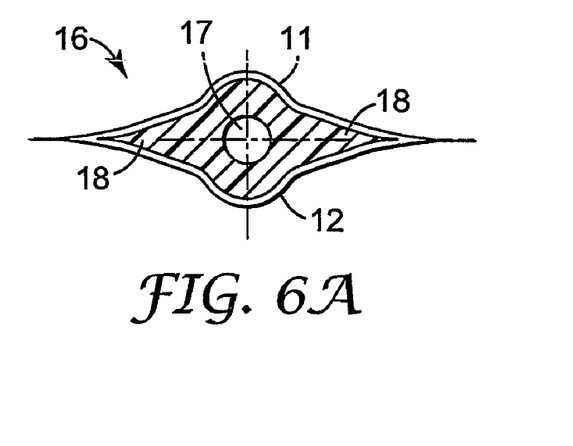
FIG. 6A shows an alternative cross-sectional structure of the extension part of the cannula.
Figure 6B:
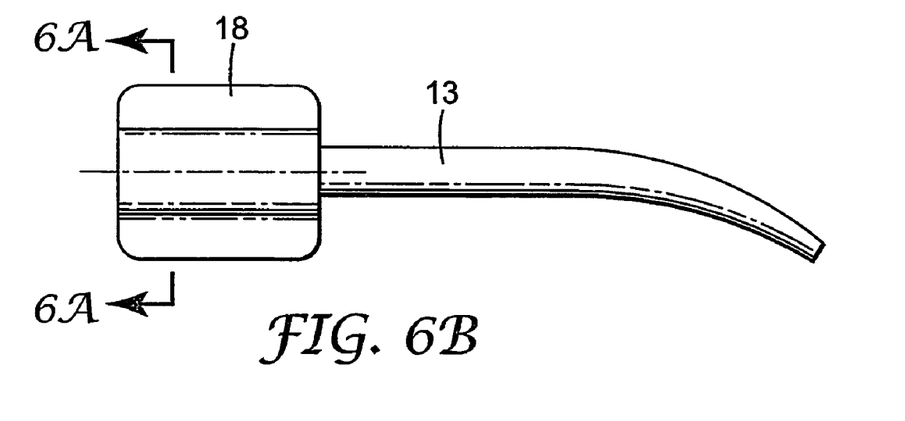
FIG. 6B shows a top view of the cannula with its extension part shown in FIG. 6A.

In order to further improve the tight seal in this area, the extension part 16 comprises fins 18 with sharp edges in the plane between the base member 11 and the cover member 12 (see FIGS. 6A and 6B). With these sharp edges, hollow spaces between the two sheets forming the base member and the cover member and the extension part of the cannula are avoided. It is clear to the skilled person that sharp edges in order to avoid hollow spaces can also be provided with cross-sectional shapes as shown in FIGS. 4 and 5, for example.

Figure 7:
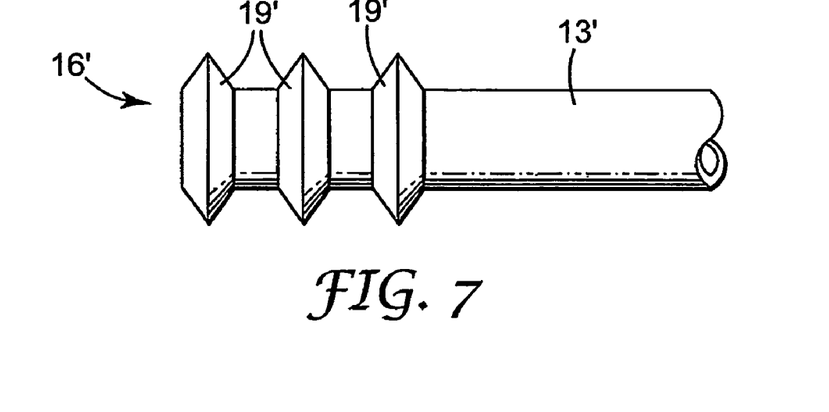
FIG. 7 shows a further alternative structure of the extension part of the cannula.

According to an alternative embodiment, as shown in FIG. 7, the extension part 16' of cannula 13' is formed like a plug containing one or more circumferential flanges 19'. Hollow spaces between the cannula and its extension part and the base member/cover member are avoided by inserting the plug-part of the cannula into the pocket area by press-fit such stretching the base member and cover member sheets around the plug. Optionally, an additional hot sealing step or gluing step (for example hot melt glue) can be applied.

Figure 8:
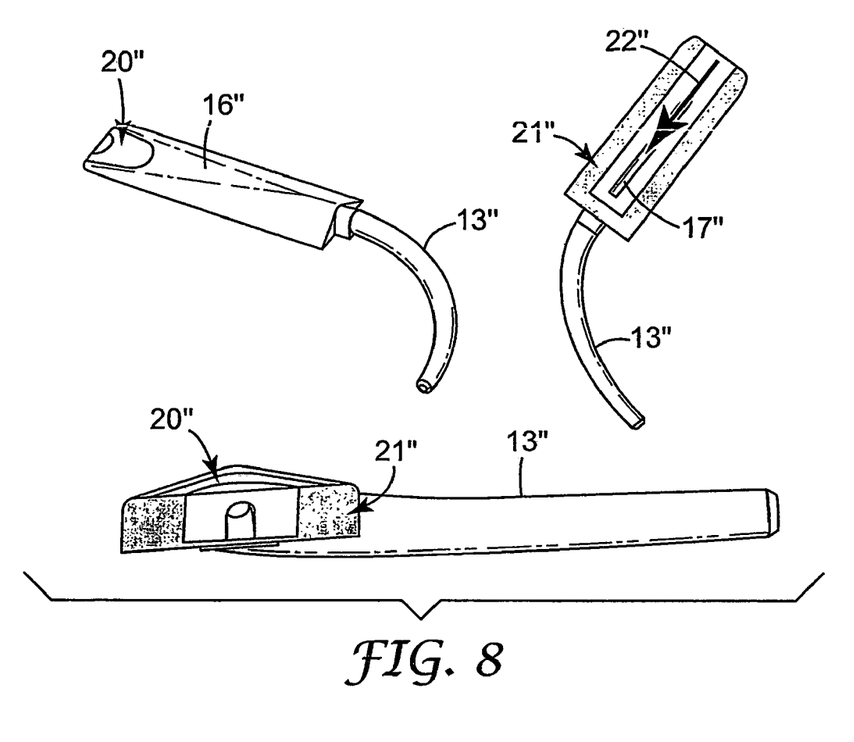
FIG. 8 shows a further alternative structure of the extension part of the cannula.

A further preferred embodiment of the extension part is shown in FIG. 8. In this embodiment, the extension part 16" has an approximately triangular cross-section in the transition area between the tubular cannula portion 13" and the extension part 16". However, towards the edge or tip of the extension part 16", the extension part 16" comprises a portion that is tapered along the length thereof. Due to the triangular cross-section, and the taper towards the end of the extension part, the resulting surface of the extension part is approximately triangularly shaped, as is clearly shown in the top left drawing of FIG. 8.

On the other side of the extension part (as shown in the top right drawing of FIG. 8), the internal passageway 17" of cannula 13" is exposed to the exterior of the cannula that an open passageway 22" is formed.

Both the upper side and the lower side of extension part 16" comprise a U-shaped sealing area, i.e. upper sealing area 20" and lower sealing area 21". The legs of these U-shaped sealing areas 20" and 21" extend towards the end of the extension part and are connected to each other at the edge of the end of the extension part 16", thus forming a continuous sealing area.

Thus, a smooth and tight transition between the flat interior of the container and the tubular cannula is provided.

Figure 9:
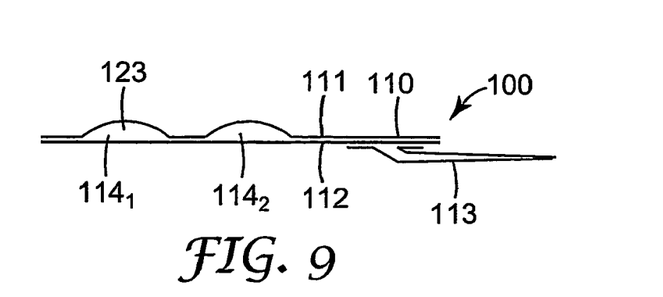
FIG. 9 shows a further aspect of the device according to the present invention with the cannula attached to the cover member of the device.

According to a further aspect of the present invention as shown in FIG. 9, device 100 comprises container 110 formed by base member 111 and cover member 112. Two compartments $114_1$ and $114_2$ are formed, containing, for example, substance 123 in compartment $114_1$. In this embodiment, cannula 113 is attached to the cover member 112 of the container 110. This embodiment is advantageous because the cannula can be attached to the cover member sheet prior to assembly of the entire container and is thus attached to the cover member at an early stage in the manufacturing process. The cover member 112 is either precut to establish a passageway, or is punched through the cannula prior to use of the device.

Figure 10:
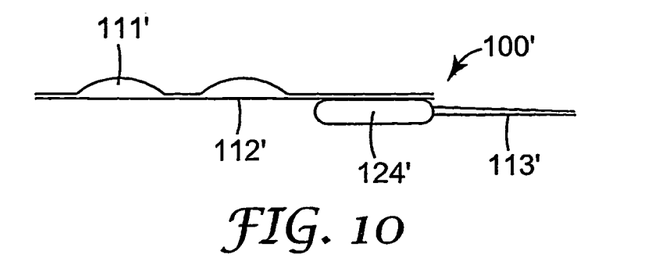
FIG. 10 shows a preferred embodiment of the device according to the present invention comprising a dosing system.

As an option, cannula 113 is provided with a separate dosing system 124' (see FIG. 10). The dosing system 124' preferably comprises a flexible volume to squeeze out the substance, or may even be provided in the form of a cartridge with a piston.

Figure 11:
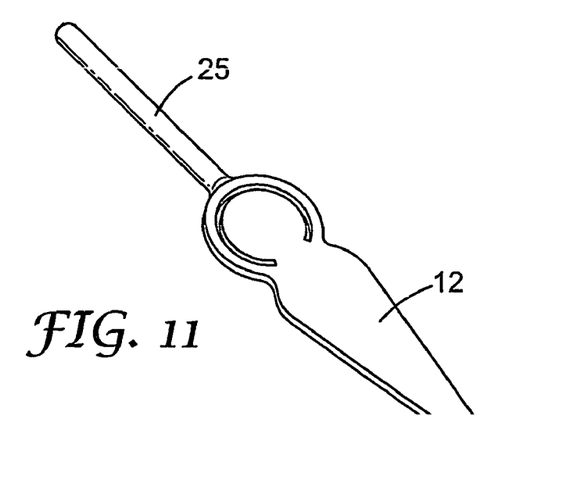
FIG. 11 shows an alternative embodiment of the device according to the present invention comprising a handle.

A further preferred option of the storage and application device according to the present invention is shown in FIG. 11. In this embodiment, the cover member 12 is a plastic part, for example an injection moulded part that has the same shape like the punching contour of the base member in order to achieve an improved stiffness, and to improve the entire handling of the device. If in this case a two- or multi-component base member is used, the plastic part forming the cover member needs to be foldable between the two compartments, for example by a line of weakness forming a hinge. FIG. 11 shows a two-compartment device. For a two-compartment design (press-fold-press-design), the first (rear) compartment has to be surrounded by a cut, e.g., a circular 300° (270°-330°) cut to enable folding of the first compartment after being pressed. This circular cut is also shown in FIG. 11. The plastic part is then sealed against the base member within the circular cut in order to avoid leakage through the cut.

It is also preferred that the plastic part 25 forms the inner layer of a foil-plastic-foil sandwich design.

As shown in FIG. 11, the plastic part also preferably comprises a handle 25.

Figure 12:
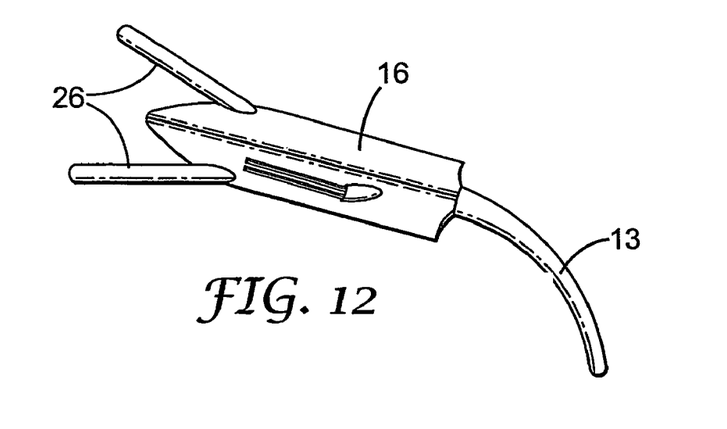
FIG. 12 shows a preferred embodiment of the device according to the present invention, wherein the extension part of the cannula comprises stiffening structure.

In order to provide a sufficient rigidity of the entire container, the base member comprises an additional strengthening or stiffening structure. Alternatively or in addition, stiffening members are included into the cannula. In the embodiment shown in FIG. 12, extension part 16 comprises stiffening members 26 that extend beyond the rear end of the extension part like feelers.

Figure 13:
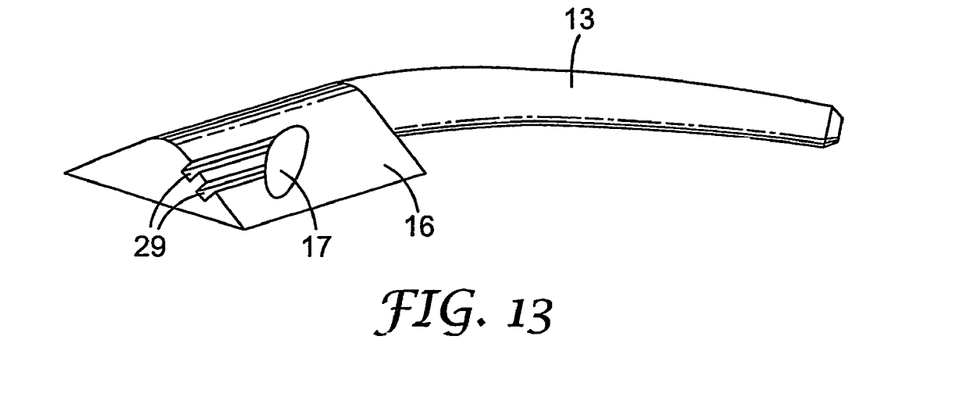
FIG. 13 shows in detail the internal passageway opening at the extension part.

As shown in FIG. 13, extension part 16 is preferably formed such that the opening of the internal passageway 17 of the cannula 13 opens at a side surface of the extension part, i.e. offset from the longitudinal axis of the cannula. According to a preferred embodiment, grooves 29 are provided in the surface at which the passageway opening is located. The grooves extend from the passageway opening towards the end of the cannula, and provide flow channels between the pocket area and the passageway.

Figure 16:
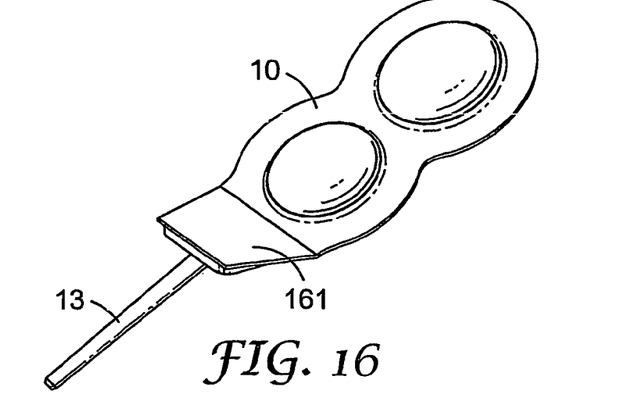
FIG. 16 shows a further preferred embodiment of the present invention with a bended extension part and a cannula in zig-zag-configuration.

FIG. 16 shows an alternative embodiment of the dispensing device according to the present invention. According to this embodiment, the cannula 13 comprises at its first end an extension part 161 adapted for being attached to the outer surface of the container 10, and preferably to the cover member 12 (see FIG. 17). For example, the extension part comprises a disk-like shape. Preferably, the disk-like extensions part 161 is attachable at one surface thereof to the container 10, and comprises the cannula 13 at the opposite side. Thus, the internal passageway of the cannula also passes through the extension part 161.

Figure 18:
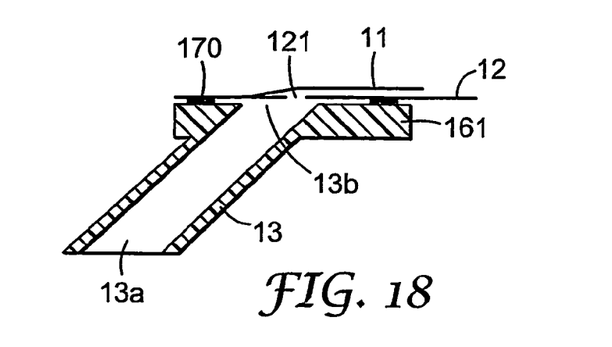
FIG. 18 shows a schematic cross-sectional view of the rear end of the cannula with extension part being attached to the container.
Figures 19, 20:
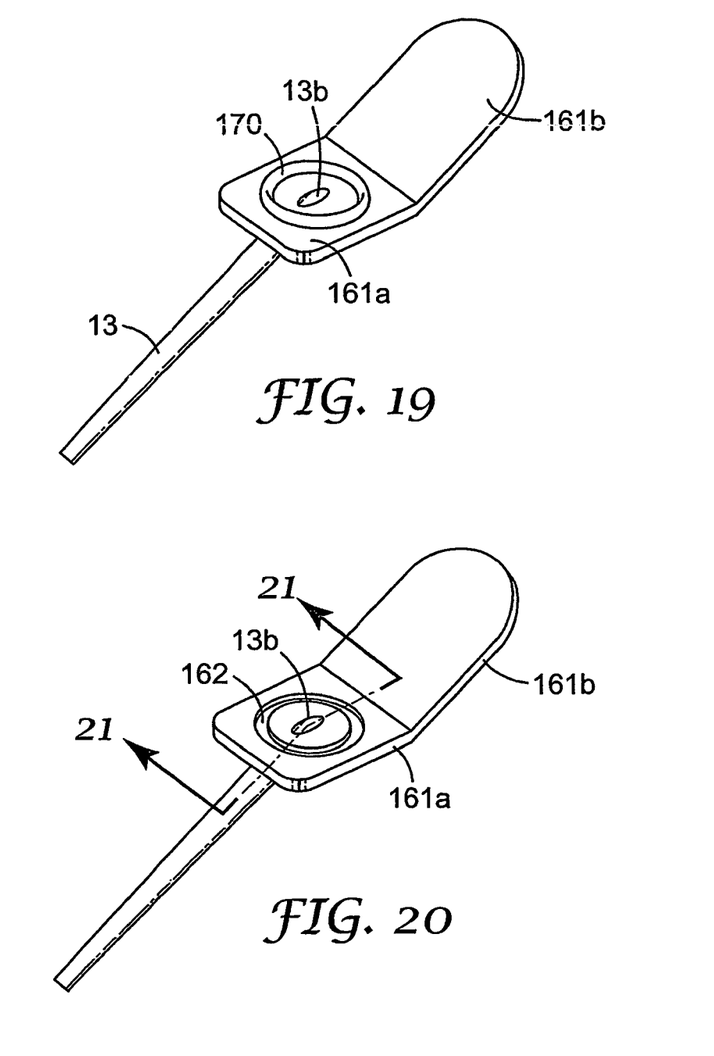
FIG. 19 shows a first alternative way of attaching the extension part to the container.
FIG. 20 shows a second alternative way of attaching the extension part to the container.
Figure 21:
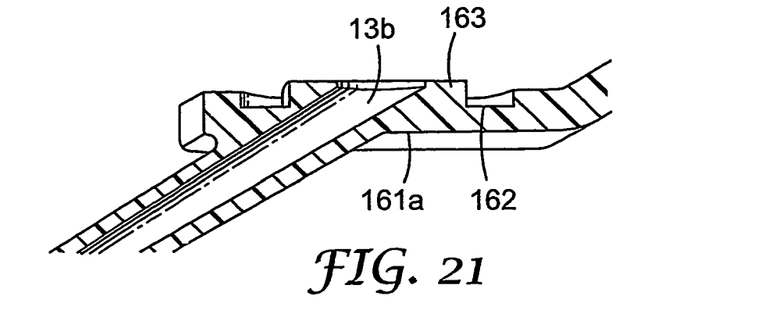
FIG. 21 shows a third alternative way of attaching the extension part to the container.

Preferably, the extension part 161 is attached to the container 10 by an adhesive or glue, respectively, which is, for example, is provided in the form of a ring at a certain distance around the passageway opening 13b at the first end. This is shown in FIGS. 18 and 19. Preferably, the ring 170 of glue is applied on the surface of the (e.g. disk-shaped) extension part 161. Alternatively, see FIG. 20, the extension part 161 comprises a recess 162, preferably ring-shaped, in the surface of that part 161a that is to be attached to the container 10; the recess 162 is adapted to receive the adhesive. The latter alternative is advantageous in that it prevents closing of the passageway by the glue. This can be further enhanced in that the part 163 of the extension part 161a surrounding the passageway outlet 13b is somewhat raised relative to the rest of the surface of the extension part, and the recess 162 surrounds the raised part 163 (see FIG. 21).

The advantage of having a "dispenser part" being formed by the cannula 13 and the extension part 161 that is attachable to the container 10 is that the container, for example a blister package, can be manufactured using existing equipment and existing processes. This provides proven quality of the container. The pre-manufactured container can then be combined with the "dispenser part" in a downstream step of the manufacturing line.

It is preferred that the cannula 13 is inclined with regard to the extension part 161, as clearly shown in FIGS. 16 to 21. That means, for example in case of a disk-shaped extension part, the cannula 13 does not perpendicularly extend from the surface of the extension part but is slightly inclined relative to the plane of the extension part. More preferably, the extension part comprises a bend 161c so that it comprises two portions 161a and 161b that are inclined relative to each other. Most preferably, the bend 161c is provided such that the entire assembly of cannula and extension part comprises a zig-zag-configuration. Such a zig-zag-configuration facilitates manufacturing of the dispenser part by injection moulding. Furthermore, it allows the entire device to be built as a non-angled device which can be handled by a user like a pen when a liquid is to be dispensed.

Figure 17:
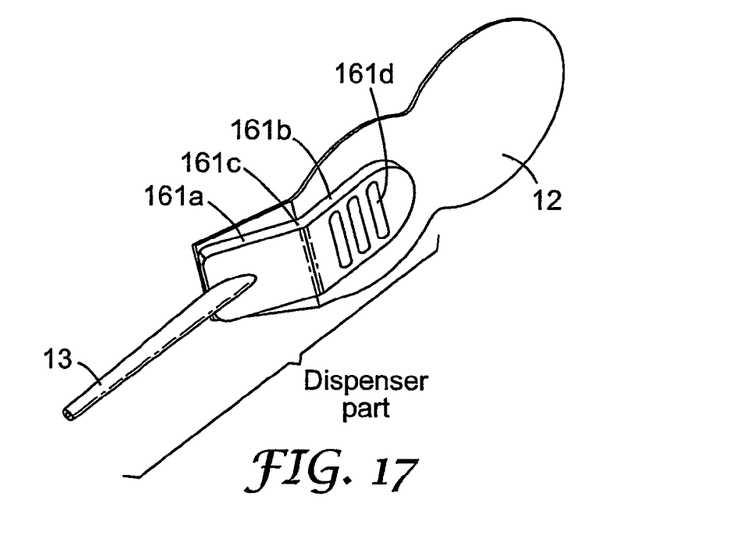
FIG. 17 shows the gripping function of the extension part.

In case the extension part 161 is attached to the cover member 12 of the container 10 as shown, e.g., in FIGS. 17 and 18, fluid communication is established, for example, by puncturing the cover member 12, for example by a small needle. It is preferred that the size of the hole 121 in the cover member 12 is smaller than the passageway of the cannula 13 because then a controlled dispensing of the substance is achievable. Furthermore, unintended all at once emptying of the container 10 is prevented.

Preferably, the extension part 161 provides a gripping function so that the dispensing device can be gripped by the user at the extension part 161. For example, as shown in FIG. 17, portion 116b of extension part 161 comprises a plurality of ribs 161d.

Figure 14:
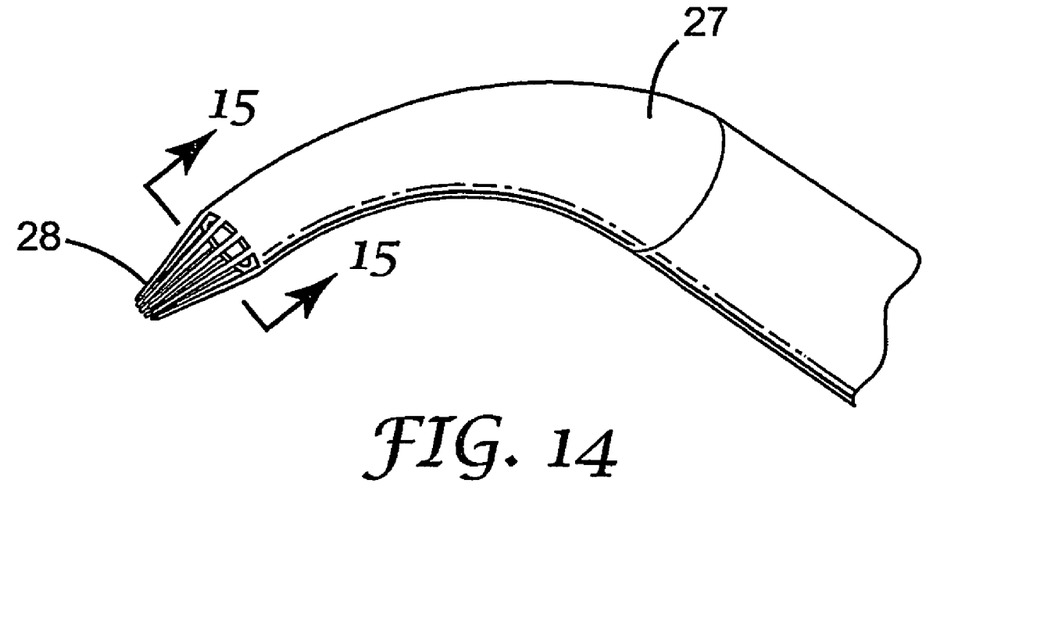
FIG. 14 shows a preferred embodiment of the device according to the present invention wherein the second end of the cannula comprises bristles.
Figure 15:
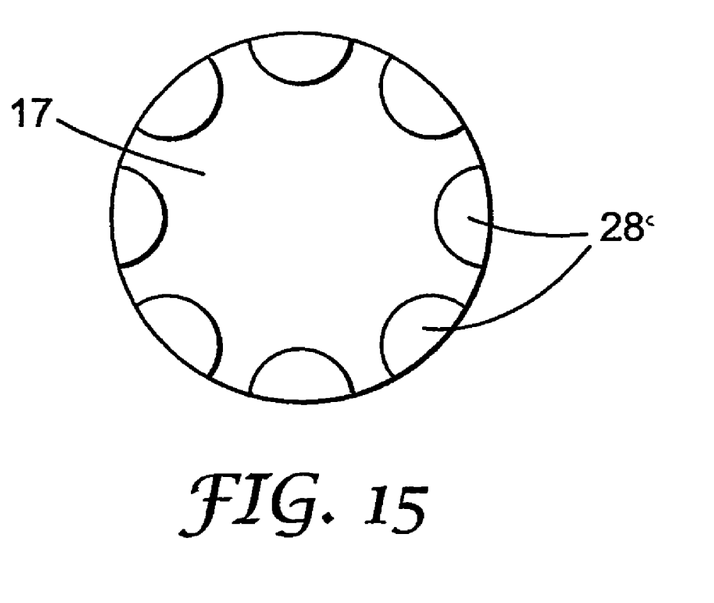
FIG. 15 shows a cross-sectional view of the application bristles at the second end of the cannula.

In all aspects of the present invention, the cannula further comprises an applicator at its second end for applying the substance to a target or treatment area. Preferably, as shown in FIG. 14, the applicator 27 comprises bristles that are (preferably integrally) formed at the second end at the cannula to form a brush for applying dispensed material to the target or treatment area. In case the bristles are integrally formed with the cannula tip, it is possible to mould the bristles and to stretch the bristles within the injection moulding tool during mould opening. In order to facilitate injection moulding, the cross-sections of the bristles are shaped as shown in FIG. 15.

In general, the shape of the compartment 14 may be circular as shown in FIGS. 1 through 3 or may have any other geometric form. The pocket 15 for receiving the cannula 13 is formed as a blind hole, which, in the storing condition, is closed to the compartment 14. Compartment 14 and the pocket 15 are arranged with respect to each other preferably such that the axis defined by the pocket 16 and cannula 13 points to the centre of the compartment 14.

The separation between the compartment 14 and the pocket 15 is designed with respect to spacing and strength of adherence between the base member 11 and cover member 12 so that a pre-defined break zone is created. With a view to minimum manufacture expenditure, the sheets forming the base member and the cover member are interconnected in the pre-defined break zone in the same way as in the outer areas, e.g., by hot sealing or gluing. In case of sealing, the pre-defined break zone may be produced by using a different, specifically a lower temperature than in the outer connecting regions.

In use, the two sheets 11, 12 are separated in the predefined break zone to connect the compartment 14 with the pocket 15. This is preferably done by pressure on the cushion-shaped compartment 14, e.g., between the user's thumb and index finger. Such pressure not only opens the predefined break zone but at the same time reduces the compartment volume to cause the substance to flow into the pocket 15 through the connection thus created, thereby providing a flow of the substance into the internal passageway of cannula 13.

The device described above is particularly suitable for storing and dispensing small liquid quantities, such as dental substances which are required for a single application in amounts of a few tenths of a milliliter. In such a case, the compartment 14 has a diameter of 10 to 15 mm in the embodiment shown, and the cannula 13 has a diameter of, e.g., >2 mm at the fixed end and approximately 0.8 mm at the second end.

In case a two- or multi-component device is used, the two or more compartments are separated from each other by a pre-defined break zone in a manner similar to the separation between the compartment 14 and the pocket 15. In use, in case of a two-compartment device, pressure is first applied to the outer compartment to connect it with the inner compartment and mix the components contained in these compartments. The part of the device comprising the emptied compartment is then folded upon the other compartments such that the compartments contact each other at the side of the cover sheet 12. By exerting pressure on the other compartment after mixing the components, the passage between the pocket and the adjacent compartment is opened and the mixed substance is dispensed through the cannula. Alternatively, both compartments may be pressed empty simultaneously. An additional mixing effect can be achieved by exerting pressure alternately on the compartments after the pre-defined break zone between the compartments has been opened and before the pre-defined break zone to the pocket has been opened.

According to a further preferred embodiment, locking structures, e.g., brackets or clips, are provided that prevent that the one compartment being folded on the other compartment moves back to its original position. In other words, the locking structure keeps the compartments close to each other at or after dispensing of the substance.

The invention claimed is:

1. A device for storing and dispensing a flowable substance, comprising:
    a container comprising
        a base member and a cover member being sealingly connected with each other along the circumference of the container, wherein said base member is formed as a sheet,
        at least one compartment for receiving said substance, and
        an open ended pocket area into which said substance is transferable from said at least one compartment, and
    a cannula having an internal passageway being in a fluid communication with said pocket for dispensing said substance, wherein said cannula is a separate component having a first end and a second end, said first end being adapted for insertion into said open end of said pocket area, and
    a portion separating said compartment from said pocket, said separating portion comprising a passage area adapted to be selectively opened by pressure effective on said passage area for placing said compartment in communication with said pocket.

2. The device of claim 1, wherein said first end comprises an extension part having a portion with an increased cross-section.

3. The device of claim 2, said extension part having a cross-sectional shape comprising sharp edges in the plane between the base member and the cover member, and preferably comprises a rhombic or fin-like cross-sectional shape.

4. The device of claim 1, wherein said extension part comprises at least one portion having an increased diameter.

5. The device of claim 1, wherein said extension part comprises a portion being tapered along the length thereof, with the thickness of the tapered portion decreasing towards said first end.

6. The device of claim 5, wherein said tapered portion comprises an U-shaped sealing area on each of the opposing surfaces of said tapered portion, the legs of said U-shaped sealing areas extending towards said first end and being connected at the edge of said first end.

7. The device of any of claims 1 to 6, wherein said first end is attached to said open ended pocket area by a heat seal, a press fit, and/or an adhesive.

8. The device of claim 1, wherein said first end comprises an extension part adapted for being attached to the outer surface of said container.

9. The device of claim 8, wherein said extension part is attachable to said cover member.

10. The device of claim 8, wherein said extension part comprises a first portion and a second portion being inclined relative to said first portion.

11. The device of claim 8, 9, or 10, wherein said cannula is inclined relative to said extension part.

12. The device of any of claims 8 to 10, wherein said internal passageway of said cannula extends through said extension part.

13. The device of claim 12, wherein said extension part comprises a recess in the surface that is attachable to said container, said recess being adjacent to and surrounding said passageway opening.

14. The device of claim 13, wherein said recess is ring shaped.

15. The device of claim 13, wherein said extension part comprises a raised portion adjacent to and surrounding said passageway opening, said recess surrounding said raised area.

16. The device of claim 1, said separate cannula being attached to said cover member, whereby said fluid communication with said pocket is established through said cover member.

17. The device of claim 16, wherein said cannula comprises a dosing system having a variable volume, preferably a bellow.

18. The device of claim 17, wherein said cannula further comprises an applicator at said second end for applying said substance to a treatment area.

19. The device of claim 18, wherein said applicator comprises bristles being integrally formed with said second end of said cannula, or comprises a foamed material, a non-woven material, or a plurality of fibres incorporated into said second end of said cannula.

20. The device of claim 19, wherein said internal passageway of said cannula further comprises flow resistors, preferably formed by structured surfaces, constricted portions, and/or orifices.

21. The device of any of claims 2 to 6, said extension part further comprising stiffening elements extending away from said extension part.

22. The device of claim 1, wherein said base member sheet is a deep-drawn sheet formed of a polypropylene layer, an aluminium layer, and a polyethylene layer.

23. The device of claim 1, said cover member being formed as a sheet, preferably being formed of a polyethylene terephthalate layer, an aluminium layer, and a polyethylene layer.

24. The device of claim 1, said cover member being formed as a plastic part, preferably as an injection moulded part.

25. The device of claim 1, comprising two or more compartments for holding different substances, and a passage area adapted to be selectively opened for placing said compartments in communication with each other prior to dispensing the mixed final substance.

26. The device of claim 1, said cannula further comprising a mixer.

27. The device of claim 26, said mixer comprising mixing helixes or elements providing flow resistance.

28. The device of claim 1, further comprising a handle.

29. The device of claim 1, wherein the container is pre-filled.

30. The device according to claim 1, in combination with a separate applicator.

31. The device according to claim 1 interconnected to at least one further device according to claim 1.

32. The device according to claim 31, wherein the device is filled with a substance, and wherein at least one of the further devices is filled with a different substance.

* * * * *

UNITED STATES PATENT AND TRADEMARK OFFICE
CERTIFICATE OF CORRECTION

PATENT NO. : 7,607,534 B2
APPLICATION NO. : 10/576910
DATED : October 27, 2009
INVENTOR(S) : Peuker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 167 days.

Signed and Sealed this

Twelfth Day of October, 2010

David J. Kappos
*Director of the United States Patent and Trademark Office*

UNITED STATES PATENT AND TRADEMARK OFFICE
CERTIFICATE OF CORRECTION

PATENT NO. : 7,607,534 B2
APPLICATION NO. : 10/576910
DATED : October 27, 2009
INVENTOR(S) : Marc Peuker It is certified that error appears in the above-identified patent and that said Letters Patent is hereby corrected as shown below:

Title Page
Column 1 (Assignee); Line 1-2, Delete "3M Innovative Properties Company, St. Paul, MN (US)" and insert -- 3M ESPE AG, Seefeld, Germany --, therefor.

On the Title Page:

The first or sole Notice should read --

Subject to any disclaimer, the term of this patent is extended or adjusted under 35 U.S.C. 154(b) by 167 days.

Column 2
Line 7; Below "said container." insert -- Preferably, the first end comprises an extension part having a portion with an increased cross-section (compared to the cross-section of the other part of the cannula). A preferred solution is thus to, for example, injection mould a cannula with a tip at one end and an extension part at the opposite end. The extension part is used for attaching the cannula tightly to the container. Preferably, the cannula is inserted into said pocket of said container in order to establish said fluid communication between said pocket and said cannula. -- as a new paragraph.

Line 18-28; Below "cover member." delete "Preferably, the extension part has a cross-sectional shape comprising sharp edges in the plane between the base member and the cover member, and more preferably comprises a rhombic, triangular or fin-like cross-sectional shape. This cross-sectional shape (in a plane perpendicular to the longitudinal axis of the cannula) of the extension part provides a smooth transition between the extension part and the surrounding base and cover member, and the sharp edges help to avoid hollow spaces between the base member and the cover member, because the sharp edges lay in the plane between the base and the cover member.".

Signed and Sealed this

Nineteenth Day of October, 2010

David J. Kappos
*Director of the United States Patent and Trademark Office*

Column 8
Line 63; Delete "precut" and insert -- pre-cut --, therefor.

Column 10
Line 36; Delete "116b" and insert -- 161b --, therefor.